United States Patent [19]

Bax

[11] 4,366,575

[45] Dec. 28, 1982

[54] METHOD AND APPARATUS FOR CONTROLLING X-RAY TUBE EMISSIONS

[75] Inventor: Ronald F. Bax, Columbia, Md.

[73] Assignee: Pfizer Inc., New York, N.Y.

[21] Appl. No.: 305,842

[22] Filed: Sep. 25, 1981

Related U.S. Application Data

[63] Continuation of Ser. No. 75,187, Sep. 13, 1979, abandoned.

[51] Int. Cl.$^3$ .......................... A61B 6/00; H05G 1/26
[52] U.S. Cl. .................................... 378/110; 378/112; 378/16
[58] Field of Search ............ 250/401, 409, 408, 445 T

[56] References Cited

U.S. PATENT DOCUMENTS

| | | | |
|---|---|---|---|
| 2,343,729 | 3/1944 | Atlee et al. | 250/401 |
| 2,667,587 | 1/1954 | Kuntke et al. | 250/408 |
| 4,101,773 | 7/1978 | Le May | 250/401 |

FOREIGN PATENT DOCUMENTS 1639397 1/1968 Fed. Rep. of Germany.

Primary Examiner—Alfred E. Smith
Assistant Examiner—T. N. Grigsby
Attorney, Agent, or Firm—Cushman, Darby & Cushman

[57] ABSTRACT

Method and apparatus for rapidly achieving stabilized x-ray emissions from an x-ray tube are disclosed. The essentially constant current characteristics of an x-ray tube are utilized so as to initially establish relatively low voltage but approximately full current, operating conditions in the x-ray tube during an initial tube preparation time period. Any relatively low energy x-rays emitted during this initial period are of little concern since they are readily absorbed in the usual beam hardening materials placed in the x-ray path. Once the x-ray tube has been stabilized at such relatively low energy output, the operating voltage may thereafter be very rapidly raised to normal operating levels while permitting concurrent rapid stabilization of the relatively small corresponding further required increase in x-ray tube current which, in turn, provides for rapid stabilization of the useful high energy x-ray tube emissions.

19 Claims, 6 Drawing Figures

METHOD AND APPARATUS FOR CONTROLLING X-RAY TUBE EMISSIONS

This is a continuation of application Ser. No. 75,187 filed Sept. 13, 1979 and now abandoned.

This invention generally relates to method and apparatus for controlling useful high energy x-ray tube emissions so as to more rapidly achieve stabiized operation at such high energy output levels. When used in medical apparatus, the invention helps minimize patient x-ray dosage and may also permit an increased useful duty cycle for the overall medical x-ray equipment in which this invention is used.

More particularly, this invention is presently intended for use in a medical CT scanner using an x-ray tube. This invention materially improves the turn on characteristics of the x-ray tube in such usages. Briefly stated, the invention exploits the typical constant current characteristics of an x-ray tube so as to speed thermal equilibrium (and resultant x-ray emission). Briefly summarized, the x-ray tube is operated during an initial preparation period so as to produce only low energy x-rays (which are ordinarily absorbed anyway by the usual beam hardening materials placed in the x-ray path) in spite of the fact that the tube is operating at approximately its final expected operating current. Once this condition has been reached, the tube voltage may be rapidly stepped to its final value (thus greatly increasing the energy of output x-rays) while the tube current (and hence output x-ray flux) may be also rapidly stabilized at its final value since it only needs to be adjusted by relatively small corresponding further required amount.

In modern CT scanner applications, the body tissues under examination often require measurements over a dynamic range of approximately 10,000 to 1. The required accuracy of such measurements made within this range is also quite high and typical requirements are one part in many thousand. Accordingly, for this particular application (and perhaps for others as well) a relatively stable x-ray flux is required from an x-ray tube during data measurements so that the useful information is not masked by variations in the x-ray output. Typically, the x-ray output flux itself must be maintained to within approximately 1% of a nominal value. Data normalization techniques are then available for making the effective stability equivalent to approximately 0.1-0.01%.

Using prior art method and apparatus for controlling x-ray tube emissions, approximately one-half second may be typically required to stabilize the x-ray flux at the required 1% of nominal value. High energy x-rays are normally output during this stabilization. As CT scan cycles become increasingly shortened (e.g. less than 5 seconds and perhaps as short as 1 or 2 seconds), this required stabilization time represents an increasingly large proportion of the total x-ray dosage suffered by the patient. Furthermore, since the x-ray tube is dissipating relatively large quantities of energy during this stabilization period, the proportion of total tube energy dissipation caused by this stabilization period also increases as the scan time is decreased thus reducing the useful duty cycle of the tube and, in some cases, limiting the number of scan cycles which may be effected over a given time span. However, using this invention, patient dosage is minimized, tube life may even be prolonged and higher patient throughput of a CT scanner system may be achieved.

In typical prior art x-ray systems, x-ray tube emission is controlled by monitoring the anode of cathode current and controlling filament temperatures in response thereto. For example, a voltage proportional to such tube current may be compared to a reference voltage and used to control the filament voltage supply. However, since the x-ray tube output is controlled by filament emission, and since the filament control loop response rate is necessarily limited by the thermal time constant of a relatively massive x-ray tube filament, stabilization delays of hundreds of milliseconds or even several seconds are typical.

One prior art technique for improving the turn on response utilizes filament preheating circuitry. Here, the filament temperature is caused to idle at a temperature slightly below the level required for normal emission and the tube is turned on by rapidly applying the required high voltage. Such prior art techniques require a compromise since a high preheat current will reduce filament life and since a low preheat current requires longer stabilization time and, in addition, may literally cause "stripping" of material from the filament during a turn on cycle thus causing gradual degradation of the filament emission characteristics.

Another prior art modification of the latter procedure intended to extend filament life is to step the filament loop from a relatively low preheat condition to a relatively high preheat condition just before turning on the x-ray tube high voltage. However, since there is no actual tube current during this initial increase in the filament preheat current, the filament regulator is presented with control inputs that tend to drive the filament to the absolute maximum temperature and, in fact, may actually burn the filament out if not properly limited. Using this technique, the time delay in applying the high voltage is also critical. Too long delay will result in considerable overshoot of emission while too little delay results in a filament temperature which only approaches equilibrium exponentially in an overdamped fashion. At best, optimum timing must be individually adjusted for each x-ray tube.

Yet another prior art modification of the just mentioned technique is to provide a memory (preferably digital) to store the last used filament voltage or current parameters and to use these values as the starting point for setting the filament control loop at the initiation of the next scan cycle. It should be appreciated, that this technique can become fairly complex in practical implementation.

Now, however, with the present invention, it has been discovered that a relatively simple method and apparatus may be provided to control x-ray tube emissions more rapidly and accurately than heretofore was possible. This discovery exploits the approximately constant current (versus voltage) characteristics of x-ray tubes. The discovery also exploits the fact that relatively "soft" low energy x-rays do not penetrate even thin aluminum filters (or other appropriate material barriers) normally placed in the path of x-rays. In accordance with this invention, the x-ray tube is initially operated during a pre-turn on period at a point where approximately full tube current is achieved but where only relatively low tube voltage is used. Thus the output comprises only "soft" x-rays which are normally harmless since they are absorbed by the usual aluminum "hardening" filters. Accordingly, the time required to reach this initial operating point on the x-ray tube is virtually immaterial. Thereafter, the tube may be very rapidly stabilized with high energy output x-rays by stepping the tube voltage up to a higher level. The required further minor adjustment and stabilization of the tube current can be rapidly effected since only minor adjustments are required. For example, rather than the typical requirement of one-half second or so to normalize high energy output x-rays with prior art approaches, this invention makes it possible to stabilize the high energy output x-rays in only approximately one-tenth second or less thus greatly reducing patient dosage and providing other advantages as will be discussed in more detail below.

These and other objects and advantages of this invention will be more completely understood and appreciated by reading the following detailed description of the presently preferred exemplary embodiment of the invention together with the accompanying drawings, of which:

Figure 1:
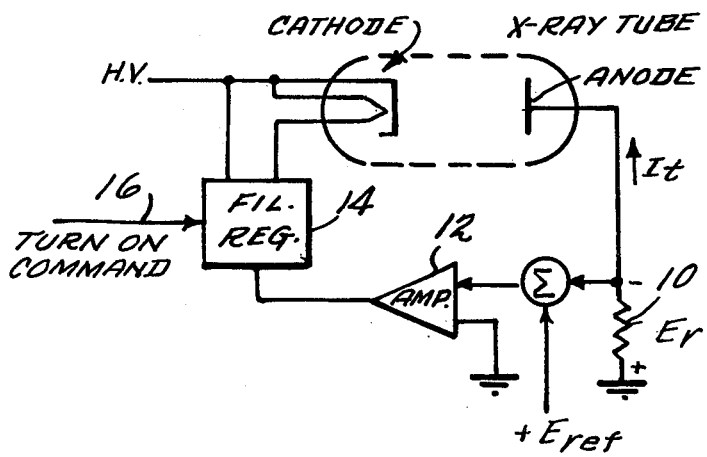
FIG. 1 is a schematic diagram of a typical prior art x-ray tube filament control loop.

As shown in FIG. 1, most prior art x-ray systems control x-ray tube emission by monitoring the anode or cathode current $I_t$ and controlling the tube filament temperature in response thereto. A measured voltage $E_r$ sensed across resistor 10 is compared to a reference voltage $E_{ref}$ and the resultant control signal (e.g. output from amplifier 12) is used to control a regulated filament supply circuit 14. The filament supply 14 is activated by a conventional turn on command at 16 as should be apparent.

If the output of amplifier 12 is negative, the filament regulator 14 increases the filament temperature to increase the x-ray tube emission (and anode current). On the other hand, the output of amplifier 12 is positive, the filament regulator reduces the filament voltage (and current) thus decreasing x-ray emissions. Since the x-ray tube emission is controlled by controlling the filament emission, the response rate is necessarily limited by the thermal time constant of the x-ray tube filament. Typically, such filaments are rather massive in size and have considerable thermal time constants thus causing turn on stabilization delays of hundreds of milliseconds or several seconds.

As already briefly discussed above, one prior art technique for improving upon the situation is to provide a filament preheat. As also discussed above, one type of prior art filament preheat technique is to initially step the filament to a higher preheat just before applying high voltage to the x-ray tube. Typically, this initial higher preheat filament current is controlled by prior art control loops such as shown in FIG. 1. It should be apparent from FIG. 1, since there is no tube current flowing without applied high voltage, the output of amplifier 12 will be at a maximum thus driving filament regulator 14 to its maximum output and the filament itself to a maximum temperature. Appropriate limiting techniques must be employed to keep the filament from burning out.

Figure 2:
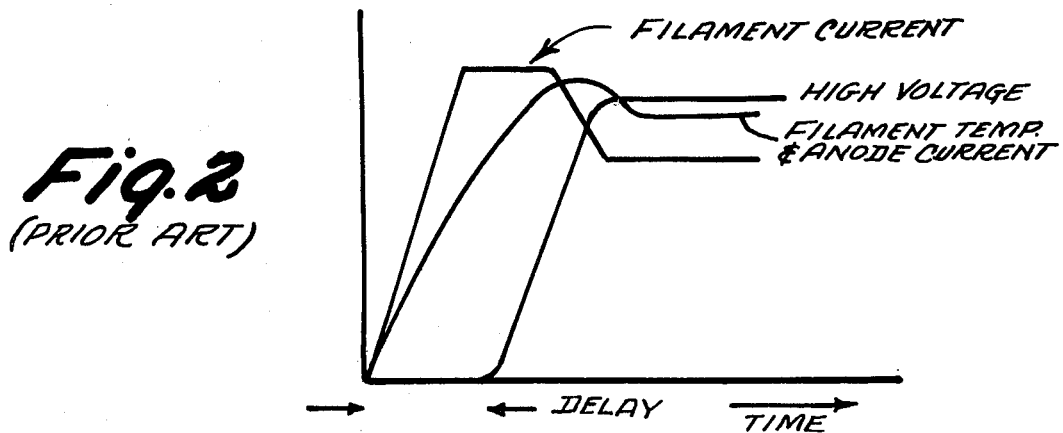
FIG. 2 is a graph showing a typical sequence of voltages and currents in prior art x-ray tube turn on techniques.

The resulting situation is depicted in FIG. 2. If the delay period shown in FIG. 2 is chosen optimally for the particular tube then in use, the filament emission may be stabilized in a relatively short time after application of the high voltage. However, as briefly discussed above, too long a time delay (for the particular tube characteristics then used in the equipment) will result in overshooting the desired x-ray emission level and too little delay will result in a filament temperature which only approaches equilibrium exponentially in an overdamped fashion. In short, the timing is critical and must be individually adjusted for each tube.

In a high speed x-ray CT scanner, the total scan time may be in the neighborhood of 1–5 seconds or less. In such an environment, the turn on delay experienced with such prior art techniques can have a substantial adverse impact. For example, unless the x-ray tube has reached a stabilized emission before data measurements are actually taken, the x-ray detectors will provide incorrect data and the resulting reconstructed tomographic image of body tissues will be incorrect. (Use of a data normalizing (reference) detector can help alleviate this adverse effect.) Furthermore, in a high speed CT scanner, the x-ray tube is typically of the rotating anode variety and can thus only store a limited quantity of "heat units" (watt/seconds, joules, btu's, etc.) before destructive heating occurs. Cooling is always marginal since it primarily depends upon radiation from the rotating anode. Typically, real time measurement or calculation of the instantaneous quantity of stored "heat units" must be accomplished so as to insure an adequate safety margin such as by disabling the entire CT scanner until such time as the stored "heat units" are back within the required safety margins. Clearly, prior art stabilization techniques which cause substantial heating during stabilization undesirably contribute to this heating problem.

Figure 3:
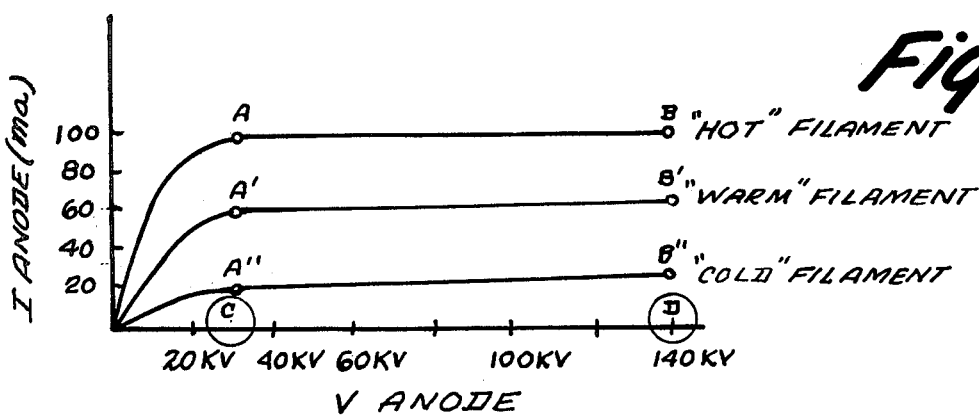
FIG. 3 is a graph showing the approximately constant current (versus voltage) characteristics of an x-ray tube for various filament temperatures.

The current versus voltage characteristics for a typical x-ray tube used in a CT scanner are shown in FIG. 3. It should be noted that, in the region above approximately 30 kv, the incremental change of current versus incremental changes of voltage is relatively small. Accordingly, if the x-ray tube is initially stabilized at an operating point A near the knee of these constant current curves, it may thereafter be rapidly stabilized at another operating point B since only relatively small current changes are required. This type of turn on operation is quite usable in CT scanners or other medical devices even if significant time is required to achieve operating point A since the "soft" 30 kv x-rays emitted at this operating point are normally lost or absorbed in the usual ⅛ inch aluminum or other metal shields normally placed in the path of x-rays. For example, such shields are normally placed in CT scanners so as to "harden" the x-ray tube output by removing any "soft" components of the x-ray emissions. These emissions would only produce unnecessary patient dosage anyway because they would never completely traverse the patient's tissue and reach the x-ray detectors disposed on the opposite side of such tissue.

Figure 4:
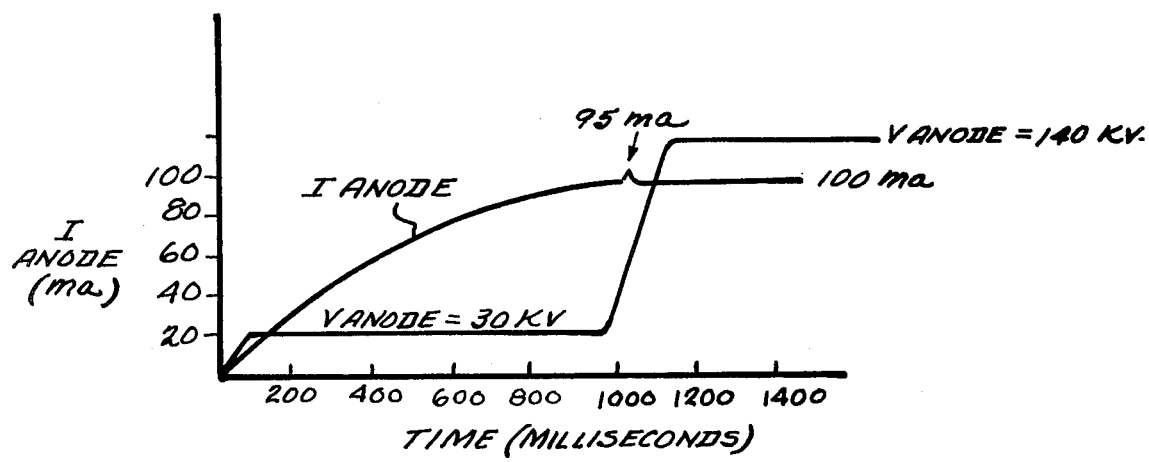
FIG. 4 is a graph showing the sequence of x-ray tube voltage and currents employed in accordance with an exemplary embodiment of this invention.

Operation of an x-ray tube in accordance with the exemplary embodiment of this invention is depicted in FIG. 4. Here, an initial tube preparation time period of 0-1,000 milliseconds is provided for stabilizing the tube operation at point A (95 milliamperes, 30 kv, constant filament temperature). During this time period, the total tube energy dissipation is approximately 18 kilowatt seconds. This is approximately only 13% of the normal energy dissipated in a 5 second scan with the tube operating at its full operating voltage of 140 kilovolts at 100 milliamperes. Stated differently, approximately 80 kilowatt seconds would be dissipated in the tube before equilibrium if one tries to simultaneously apply full operating voltage and current to the tube. Accordingly, as compared to this situation, the invention has saved approximately 62 kilowatt seconds of energy dissipation.

At the end of this initial tube preparation time period (e.g. 1-2 seconds), the tube may be dissipating on the order of 28,500 watts since less than 1% of the applied energy is converted to x-rays at this low 30 kv anode voltage. Thereafter when tube turn on is desired, the voltage is stepped as rapidly as possible to its full value (140-150 kv). Typically available voltage regulator systems can achieve voltage swings at rates on the order of $10^6$ volts per second which is much more rapid than the control rate which may be achieved in a filament control loop. As the voltage is stepped from approximately 30 kv to 140 kv, the tube operating point is similarly changed from point A to point B. (The constantly maintained filament temperature will determined which of the several constant current curves in FIG. 3 is involved.) Since the tube current only has to shift from 95 milliamperes to approximately 100 milliamperes (a change of only 5%), even a tube with a one-half second filament thermal time constant can make the adjustment to within ±1% of the total output flux in a fairly short time. Typically, the tube can reach its equilibrium emission in approximately one-tenth to one-fourth of the time required for an unmodified prior art technique.

As already discussed, this improvement reduces unnecessary patient dosage and also permits a higher patient throughput (e.g. 10-20% increase or more) due to the reduced unnecessary energy dissipation required of the tube for each cycle of operation in a CT scanner. Tube life may also be prolonged over some prior art techniques since "stripping" of the filament is avoided with this invention.

Figure 5:
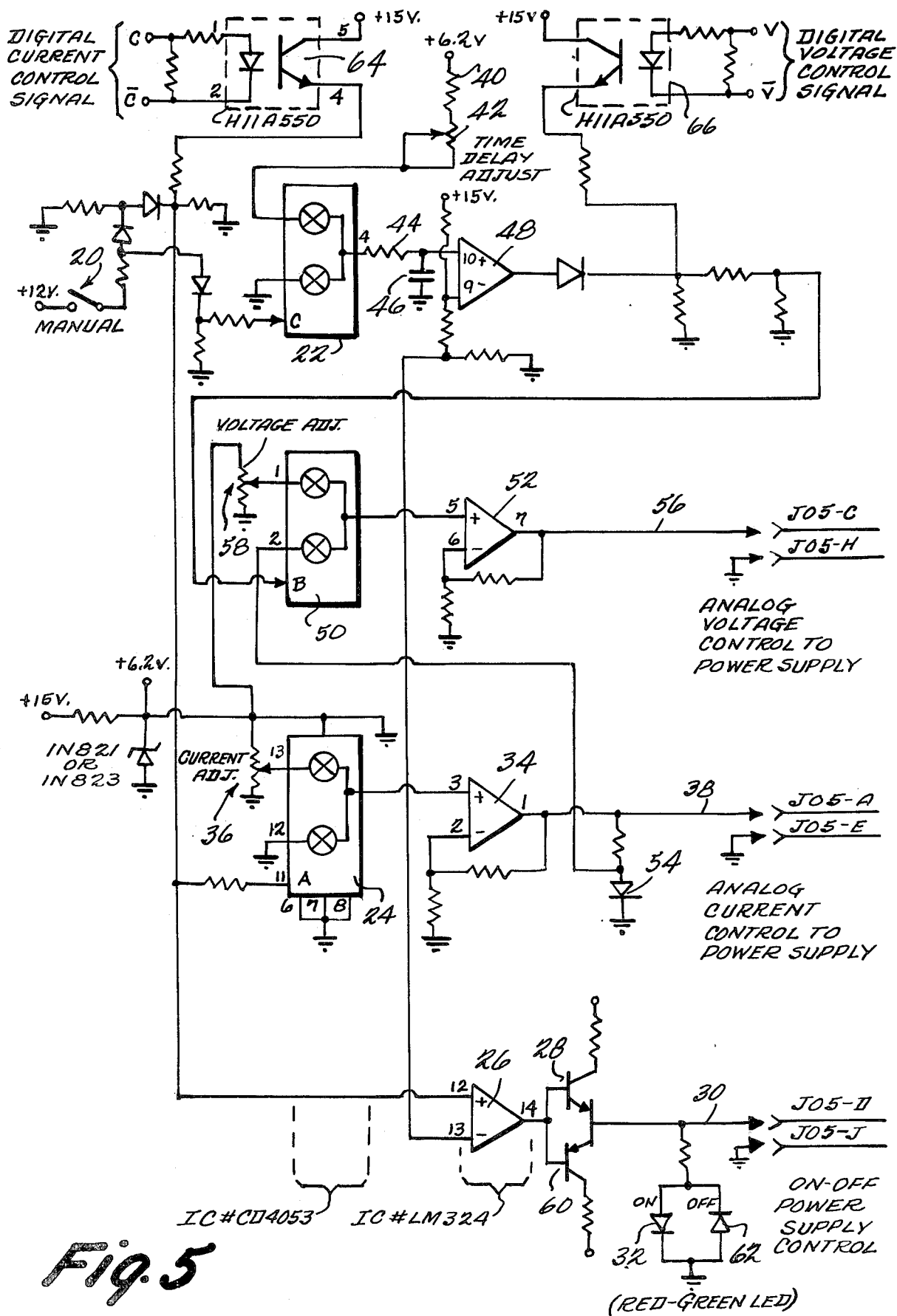
FIG. 5 is a schematic diagram of an exemplary circuit which may be used for either manually or automatically (under computer control) generating required analog voltage control signals for a suitable x-ray tube power supply from one or more discrete input signals.

An exemplary embodiment of circuitry for achieving this improved control of x-ray tube emissions is shown in FIG. 5. As shown in FIG. 5, such control may be achieved either manually through operation of switch 20 or under automatic computer control through computer provided digital control signals C, C and V, V.

The manual operation of the circuitry will first be described. As switch 20 is closed, a positive control voltage is applied to the control inputs C, A of digital SPDP switches 22 and 24 as well as to the positive input of comparator 26. This input causes the output of comparator 26 to saturate in the positive direction thus turning "on" transistor 28 and supplying an "on" power supply control signal on line 30. A red colored LED 32 is also switched on by this action to signify the activation of the power supply. In the exemplary embodiment a Delta ray model M150-100CX x-ray power supply is utilized and the terminal designations shown at the right of FIG. 5 are appropriate for that particular power supply. In general, any x-ray tube power supply may be used which provides anode and cathode voltages and currents controlled in magnitude by respectively corresponding analog signals. This particular power supply also requires an on/off control signal as applied on line 30.

The positive control signal to electronic switch 24 connects a positive input to amplifier 34 via the adjustable potentiometer 36. The output of amplifier 34 on line 38 is thus an analog current control corresponding to the final desired x-ray tube current.

At the same time, the positive control signal via manual switch 20 applied to the electronic switch 22 connects a positive voltage to an adjustable RC timing network comprising resistors 40, 42 and 44 and capacitor 46. When the output of this RC timing network exceeds the reference voltage also input to comparator 48, its output will saturate in a positive direction thus providing a positive control signal to the electronic switch 50. As should be appreciated, in this manual control mode, the RC timing network defines the relative timing of control signals applied to switches 24 and 50 and thus defines the initial tube preparation time period.

In its normal condition, (i.e. no positive control signal applied), electronic switch 50 connects a very small, substantially constant, positive input voltage to amplifier 52 via a connection to the voltage drop across diode 54 which, in turn, is forward biased due to the analog control current appearing on line 38. Thus, during the initial tube preparation period, a relatively small analog voltage control appears on line 56 corresponding to approximately 25-30 kv of x-ray tube operating voltage. However, after the initial tube preparation period has ended, a positive control signal applied to electronic switch 50 will cause the input to amplifier 52 to be increased significantly via a pre-adjustable positive supply voltage applied through adjustable potentiometer 58. At this time, the analog voltage control signal on line 56 is stepped to correspond to the full x-ray tube operating voltage (140-150 kv).

Termination of the x-ray tube operating cycle may then be manually effected by opening switch 20. This operation will cause the output of electronic switches 22 and 24 to be grounded and, at the same time, will cause the output of comparator 26 to saturate in a negative direction thus turning on transistor 60 and causing the green LED 62 to light while turning "off" the power supply control signal.

Figure 6:
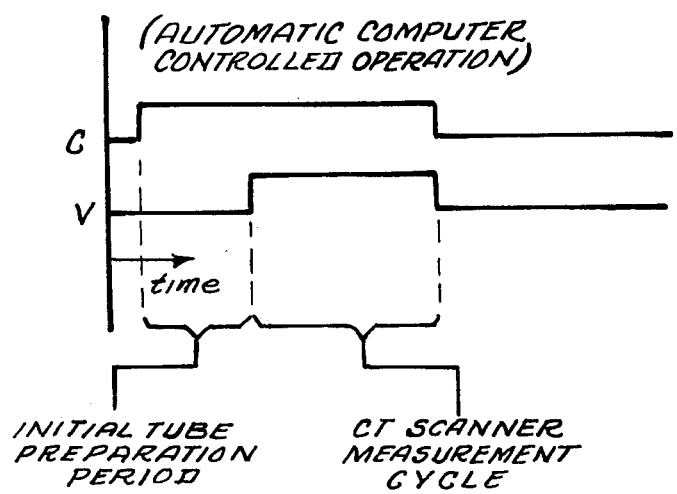
FIG. 6 is a graph of digital control signals provided to the automatic computer control operation of the circuitry shown in FIG. 5.

Automatic computer control operation may be effected by supplying digital current and voltage control signals C, C and V, V respectively as shown in FIG. 6. Here, as digital current control signal C is initially applied, the signal is transmitted through an optical coupler 64 to provide a positive control signal to electronic switch 24 and to comparator 26. Thereafter, after a suitable initial tube preparation time period, a digital voltage control signal V, V is supplied via optical coupler 66 to provide a positive control input to digital switch 50. Thereafter, operation of the digital switches, amplifiers and comparators to generate power supply, analog current and analog voltage control signals on lines 30, 38 and 56 is as already discussed for manual operation. The whole CT scanner measurement cycle may then be terminated by cessation of the digital signals C and V as shown in FIG. 6.

As indicated in FIG. 5, the electronic switches 22, 24 and 50 may be realized as a single commercially available integrated circuit CD4053. Similarly, the comparators and amplifiers 48, 26, 34 and 52 may be realized as a single commercially available integrated circuit LM324. The optical couplers 64 and 66 may, for example, be the commercially available type H11A550.

While only one specific exemplary embodiment has been described in detail, those skilled in the art will recognize that many variations and modifications of this exemplary embodiment are possible without departing from the novel and advantageous features of this invention. Accordingly, all such variations and modifications are intended to be included within the scope of this invention as defined in the appended claims.

What is claimed is:

1. Apparatus for rapidly achieving stabilized x-ray emissions from an x-ray tube having an anode and cathode, said apparatus comprising:
   voltage control means connected for initially establishing a voltage across said anode and cathode which is substantially lower than an expected final operating voltage such that only relatively low energy x-rays, if any, are emitted during an initial tube preparation time period;
   current control means connected for initially establishing a current during said preparation time period between said anode and cathode which is approximately equal to an expected final operating current and which is never substantially in excess of the expected final operating current;
   said voltage control means also including means for rapidly raising said voltage across the anode and cathode to said expected final operating voltage after said initial tube preparation period thereby permitting rapid stabilization of the relatively small corresponding further required increase in x-ray tube current which, in turn, provides the useful high energy x-ray tube emissions.

2. Apparatus as in claim 1 including an x-ray tube power supply providing anode and cathode voltage and current controlled in magnitude by respectively corresponding analog signals and wherein:
   said voltage control means and said current control means are initially activated by at least one first discrete input signal representing the beginning of said initial tube preparation period to provide, as respectively corresponding outputs, said analog signals;
   said voltage control means being further activated after said initial tube preparation period by at least one second discrete signal to step its output analog signal to a value corresponding to said expected final operating voltage.

3. Apparatus as in claim 1 or 2 wherein said voltage control means and said current control means are provided with separate digital control input ports for receiving respectively corresponding time-referenced control inputs thereat which define said initial tube preparation time period.

4. Apparatus as in claim 2 further comprising:
   a time delay circuit connected to receive said first discrete input signal and to provide said second discrete signal at a predetermined time period thereafter.

5. Apparatus as in claim 2 or 4 including further comprising an on/off power supply control circuit connected to receive said first discrete input signal and to provide on/off control signals to said x-ray tube power supply in response thereto.

6. Apparatus as in claim 2 or 4 further comprising a manual switch for manually generating said first discrete input signal.

7. A source of x-ray flux which can be rapidly stabilized in response to a turn-on command, said source comprising:
   an x-ray tube having a cathode and an anode,
   an electrical power supply connected to provide controlled levels of electrical voltage and current respectively across and through said cathode and anode, and
   a control circuit connected to control said power supply so as to initially establish first levels of voltage and current with respect to said cathode and anode with said first level of controlled current being approximately equal to a desired final second level of current and never substantially in excess of the desired final second level of current and, in response to said turn-on command, to thereafter establish second levels of stabilized voltage and current with respect to said cathode and anode.

8. A source of x-ray flux as in claim 7 wherein said x-ray tube exhibits substantially constant current versus voltage operating characteristics above some first predetermined value of voltage and wherein said first levels of voltage and current establish an operating point for said x-ray tube near said first predetermined value of voltage and wherein said second levels of voltage and current establish an operating point for said x-ray tube near a second predetermined value of voltage where x-rays of a desired usuable energy level are generated.

9. A source of x-ray flux which can be stabilized in response to a turn-on command, said source comprising:
   an x-ray tube having a cathode and an anode,
   an electrical power supply connected to provide controlled levels of electrical voltage and current respectively across and through said cathode and anode,
   a control circuit connected to control said power supply so as to initially establish first levels of voltage and current with respect to said cathode and anode and, in response to said turn-on command, to thereafter establish second levels of voltage and current with respect to said cathode and anode, and
   material placed in the path of said x-ray flux to substantially absorb any x-rays produced by the x-ray tube when provided with said first levels of voltage and current.

10. A source of x-ray flux as in claim 9 wherein said control circuit includes a time delay circuit connected to cause the establishment of said second levels of voltage and current at a predetermined time delay after said first levels of voltage and current have been applied to the x-ray tube.

11. A source of x-ray flux as in claim 9 wherein said control circuit includes separate control input ports for receiving respective input signals which independently and respectively control the establishment of said first and second levels of voltage and current.

12. Method for rapidly achieving stabilized x-ray emissions from an x-ray tube having an anode and cathode, said method comprising the steps of:
   initially establishing a voltage across said anode and cathode which is substantially lower than an expected final operating voltage such that only relatively low energy x-rays, if any, are emitted during an initial tube preparation time period;
   initially establishing a current during said preparation time period between said anode and cathode which is approximately equal to an expected final operating current and which is never substantially in excess of the expected final operating current;

rapidly raising said voltage across the anode and cathode to said expected final operating voltage after said initial tube preparation period thereby permitting rapid stabilization of the relatively small corresponding further required increase in x-ray tube current which, in turn, provides the useful high energy x-ray tube emissions.

13. Method as in claim 12 wherein a controllable x-ray tube power supply is provided to control the magnitude of cathode voltage and current by respectively corresponding analog signals and further comprising:

initially controlling the voltage magnitude in response for at least one first discrete input signal representing the beginning of said initial tube preparation period to provide, as respectively corresponding outputs, said analog signals; and further controlling the voltage magnitude after said initial tube preparation period in response to a least one second discrete signal so as to step the corresponding output analog signal to a value corresponding to said expected final operating voltage.

14. Method as in claim 12 or 13 wherein separate digital control inputs receive respectively corresponding time-referenced control inputs thereat which define said initial tube preparation time period.

15. Method as in claim 13 further comprising:
receiving said first discrete input signal and, after a predetermined time delay, providing said second discrete signal in response thereto.

16. Method as in claim 13 or 15 further comprising the generation of on/off control signals to said x-ray tube power supply in response to said first discrete input signal.

17. Method as in claim 13 or 11 wherein said first discrete input signal is manually generated.

18. A method for stabilizing x-ray flux from an x-ray tube, said method comprising the steps of:

initially establishing a relatively low voltage operating point for said x-ray tube, thereafter raising the x-ray tube operating point to its desired full operating voltage level, and absorbing in a material barrier substantially all x-rays emitted from said x-ray tube while at said relatively low voltage operating point.

19. A method for stabilizing x-ray flux from an x-ray tube, said method comprising the steps of:

initially establishing a relatively low voltage stabilized operating point for said x-ray tube with a controlled current approximately equal to the final desired full operating current level and never substantially in excess of the final desired full operating current level, and thereafter raising the x-ray tube stabilized operating point to its desired full operating voltage and current levels.

* * * * *